US011523969B2

(12) United States Patent
Vedrine

(10) Patent No.: US 11,523,969 B2
(45) Date of Patent: Dec. 13, 2022

(54) APPARATUS AND METHODS FOR SEALING A MEDICAMENT WITHIN A MEDICAL DELIVERY DEVICE

(71) Applicant: Genentech, Inc., South San Francisco, CA (US)

(72) Inventor: Lionel Vedrine, Palo Alto, CA (US)

(73) Assignee: Genentech, Inc., South San Francisco, CA (US)

(*) Notice: Subject to any disclaimer, the term of this patent is extended or adjusted under 35 U.S.C. 154(b) by 302 days.

(21) Appl. No.: 16/854,144

(22) Filed: Apr. 21, 2020

(65) Prior Publication Data

US 2020/0261314 A1  Aug. 20, 2020

Related U.S. Application Data

(62) Division of application No. 14/813,788, filed on Jul. 30, 2015, now Pat. No. 10,729,616.

(Continued)

(51) Int. Cl.
*A61J 1/14* (2006.01)
*B65B 3/00* (2006.01)
(Continued)

(52) U.S. Cl.
CPC ........... *A61J 1/1412* (2013.01); *A61J 1/1406* (2013.01); *A61J 1/1468* (2015.05); *A61M 39/20* (2013.01);
(Continued)

(58) Field of Classification Search
CPC . F26B 5/06; B65B 3/003; B65B 7/161; B65B 63/08; A61J 1/1412; A61J 1/1468; A61J 1/1406; A61M 39/20
(Continued)

(56) References Cited

U.S. PATENT DOCUMENTS 2,649,090 A   8/1953  Parsons et al.
2,668,364 A * 2/1954  Colton .................... F26B 9/066
                                                    392/416

(Continued)

FOREIGN PATENT DOCUMENTS

CN       1440350       9/2003
CN     103200922       7/2013
(Continued)

OTHER PUBLICATIONS

International Search Report for International Patent Application No. PCT/US2015/042879, dated Nov. 5, 2015.
(Continued)

*Primary Examiner* — Stephen M Gravini
(74) *Attorney, Agent, or Firm* — Weiss & Arons LLP

(57) ABSTRACT

Apparatus and methods for lyophilizing and sealing a medicament within a medical delivery device having an opening. The apparatus may include a stopper for sealing the opening. The stopper may have one or more elongated members extending from a base, in a direction that is parallel to a central axis of the base. One or more of the members may be set radially away from the axis and define a coaxial central well. The member or members may define a void. The elongated member or members may engage a device inner wall and support the base away from the opening. The void may provide gas exchange between a device interior and a device exterior. The gas may be a lyophilization byproduct that escapes from the device interior between the inner wall, the base and the member or members. The stopper may be advanced into the device to seal the opening.

20 Claims, 11 Drawing Sheets

Related U.S. Application Data

(60) Provisional application No. 62/032,752, filed on Aug. 4, 2014.

(51) Int. Cl.
  *B65B 7/16* (2006.01)
  *B65B 63/08* (2006.01)
  *A61M 39/20* (2006.01)
  *F26B 5/06* (2006.01)

(52) U.S. Cl.
  CPC .............. *B65B 3/003* (2013.01); *B65B 7/161* (2013.01); *B65B 63/08* (2013.01); *F26B 5/06* (2013.01)

(58) Field of Classification Search
  USPC .......................................................... 34/284
  See application file for complete search history.

(56) References Cited

U.S. PATENT DOCUMENTS

| | | | | |
|---|---|---|---|---|
| 3,578,195 | A * | 5/1971 | Ogle | B65D 51/241 |
| | | | | 215/307 |
| 3,901,402 | A | 8/1975 | Ayres | |
| 4,211,333 | A | 7/1980 | Villarejos | |
| 4,251,003 | A * | 2/1981 | Bodenmann | B65D 55/02 |
| | | | | 215/254 |
| 5,219,083 | A | 6/1993 | Liebert et al. | |
| 5,320,603 | A | 6/1994 | Vetter et al. | |
| 5,328,041 | A | 7/1994 | Hook et al. | |
| 5,358,491 | A | 10/1994 | Johnson et al. | |
| 5,489,266 | A * | 2/1996 | Grimard | A61M 5/284 |
| | | | | 604/82 |
| 5,727,333 | A * | 3/1998 | Folan | F26B 5/065 |
| | | | | 34/92 |
| 5,819,964 | A * | 10/1998 | Grimard | B65D 51/002 |
| | | | | 215/249 |
| 6,199,297 | B1 | 3/2001 | Wisniewski | |
| 6,352,522 | B1 | 3/2002 | Kim et al. | |
| 6,564,471 | B1 * | 5/2003 | Sutherland | F26B 5/06 |
| | | | | 34/92 |
| 6,626,870 | B1 * | 9/2003 | Yarborough | A61M 5/31511 |
| | | | | 604/199 |
| 7,334,346 | B2 * | 2/2008 | Nomine | G01N 21/68 |
| | | | | 34/92 |
| 7,708,719 | B2 | 5/2010 | Wilmot et al. | |
| 7,966,746 | B2 * | 6/2011 | Py | F26B 5/06 |
| | | | | 514/1.9 |
| 8,371,039 | B2 * | 2/2013 | Kuu | A61K 9/19 |
| | | | | 165/185 |
| 8,771,254 | B2 | 7/2014 | Nalesso et al. | |
| 9,003,676 | B2 * | 4/2015 | Yarborough | A61J 1/1412 |
| | | | | 34/287 |
| 9,828,124 | B2 * | 11/2017 | Wissner | B65B 7/2892 |
| 9,945,611 | B2 * | 4/2018 | DeMarco | F26B 5/065 |
| 10,729,616 | B2 * | 8/2020 | Vedrine | A61J 1/1468 |
| 10,809,003 | B2 * | 10/2020 | De Beer | F26B 5/06 |
| 11,054,185 | B1 * | 7/2021 | Trappier | F26B 5/06 |
| 11,135,168 | B2 * | 10/2021 | Carite | F26B 5/06 |
| 11,143,454 | B2 * | 10/2021 | Triglia, Jr. | F26B 25/22 |
| 2001/0002013 | A1 | 5/2001 | Claessens et al. | |
| 2004/0011826 | A1 | 1/2004 | Stradella | |
| 2005/0113763 | A1 * | 5/2005 | Reynolds | A61J 1/062 |
| | | | | 29/777 |
| 2007/0060877 | A1 | 3/2007 | Bassarab et al. | |
| 2012/0248057 | A1 | 10/2012 | Bogle et al. | |
| 2020/0261314 | A1 * | 8/2020 | Vedrine | A61M 39/20 |
| 2021/0180865 | A9 * | 6/2021 | Trout | F26B 5/06 |
| 2021/0325110 | A1 * | 10/2021 | Patel | F26B 5/06 |
| 2022/0096329 | A1 * | 3/2022 | Gillespie, III | A61J 1/201 |

FOREIGN PATENT DOCUMENTS

| | | | | |
|---|---|---|---|---|
| CN | 203443286 | | 2/2014 | |
| CN | 103796624 | | 5/2014 | |
| DE | 102005038368 | | 2/2007 | |
| EP | 3177359 | B1 * | 4/2020 | ............... A61J 1/00 |
| FR | 2096680 | | 2/1972 | |
| JP | 6508543 | | 9/1994 | |
| JP | 2001515435 | | 9/2001 | |
| JP | 2001-301781 | | 10/2001 | |
| JP | 2002-165861 | | 6/2002 | |
| JP | 2003-534993 | | 11/2003 | |
| JP | 2013-245834 | | 12/2013 | |
| JP | 6739356 | B2 * | 8/2020 | ............... A61J 1/00 |
| RU | 2126242 | | 2/1999 | |
| RU | 2258537 | | 12/2003 | |
| WO | WO9320869 | | 10/1993 | |
| WO | WO9717265 | | 5/1997 | |
| WO | WO00/44641 | | 8/2000 | |
| WO | WO/0044641 | | 8/2000 | |
| WO | WO01/92126 | | 12/2001 | |
| WO | WO03/039632 | | 5/2003 | |
| WO | WO2006/013360 | | 2/2006 | |
| WO | WO-2016022385 | A1 * | 2/2016 | ............... A61J 1/00 |

OTHER PUBLICATIONS

Written Opinion of the International Searching Authority for International Patent Application No. PCT/US2015/042879, dated Nov. 5, 2015.

Certified copy of English Translation of French Patent No. FR2096680, May 29, 1970.

Intellectual Property Office of Singapore Written Opinion in application No. 11201700436S, dated Jan. 11, 2018.

Federal Institute of Industrial Property in Russia, Office Action in Application No. 2016152512, dated Feb. 8, 2019.

State Intellectual Property Office of China, Office Action in Application No. 201580040261.9, dated Feb. 26, 2019.

Japanese Office Action in Application No. 2016-575899, dated Apr. 10, 2019,.

* cited by examiner

US 11,523,969 B2

APPARATUS AND METHODS FOR SEALING A MEDICAMENT WITHIN A MEDICAL DELIVERY DEVICE

CROSS-REFERENCE TO RELATED APPLICATIONS

This application claims the benefit of U.S. Provisional Application No. 62/032,752, filed on Aug. 4, 2014, which is hereby incorporated by reference herein in its entirety.

BACKGROUND OF THE INVENTION

A medicament may be delivered into a patient by syringe.

The medicament may be loaded into the syringe at the time of delivery to the patient. The medicament may be "pre-filled" into the syringe prior to packaging the syringe for use by a practitioner.

The medicament may be loaded into the syringe in an injectable form.

The medicament may be loaded into the syringe in a form or composition that requires conversion prior to injection. For example, a medicament that is loaded in a solid, crystalline, gelatinous, paste, slurry, hydrogel or liquid form may require mixing with another substance that is in solid, crystalline, gelatinous, paste, slurry, hydrogel or liquid form.

The syringe may be pre-filled with the medicament during manufacture. Pre-filled syringes are advantageous with respect to safety, accurate dosing and simplicity of use.

Some medicaments exhibit low stability in liquid form. Desiccating these medicaments, as by lyophilization, yields a dry form with higher stability. Syringes manufactured containing such dry medicament and in which the liquid injectable form can be timely reconstituted for delivery, combine the advantages of pre-filled syringes with enhanced shelf-life.

To obtain the dry form of medicament in situ within the syringe or within a syringe part (such as a tube), a medicament-containing interior of the syringe or of the syringe part is exposed to a desiccation process. Typically, the desiccation process proceeds within a setting (for example, a closed chamber) in which temperature and pressure are carefully regulated. Manufacturing syringes pre-filled with desiccated medicament is complicated by re-exposure of the medicament to airborne humidity following the desiccation process and prior to the interior being sealed off from surroundings outside the regulated setting.

It would be desirable, therefore, to provide apparatus and methods for reducing the exposure to humidity of medicament desiccated within a syringe or within a syringe part.

BRIEF DESCRIPTION OF THE DRAWINGS

FIG. 4b is another perspective view of the apparatus shown in FIG. 4a;

FIG. 11 is a partial cross-sectional view of the apparatus shown in FIG. 10a;

FIG. 14b is another perspective view of the apparatus shown in FIG. 14a;

FIG. 30b is a another perspective view of the apparatus shown FIG. 30a; and

DETAILED DESCRIPTION OF THE DISCLOSURE

Figure 1:
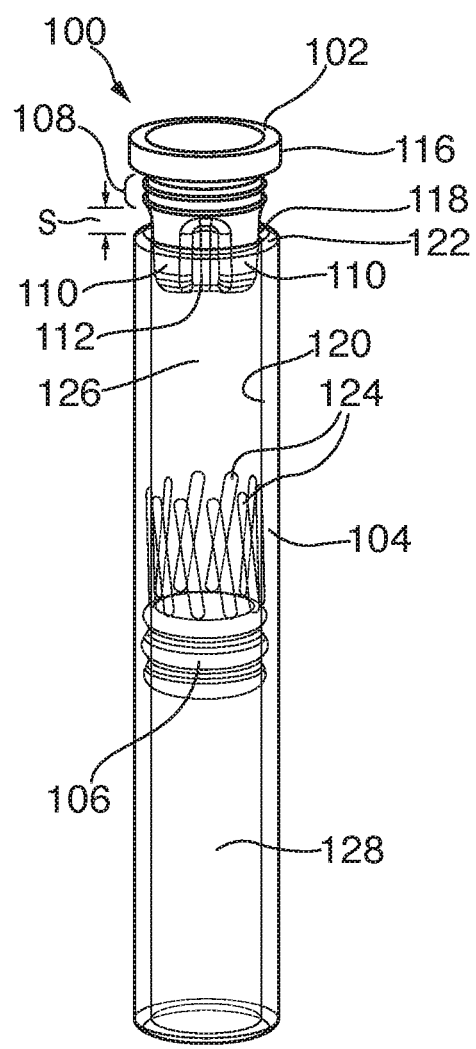
FIG. 1 is a perspective view of apparatus in accordance with the principles of the invention.

Apparatus and methods for lyophilizing and sealing a medicament within a medical delivery device are provided. The apparatus may be used to perform one or more steps of the methods. The apparatus and methods may provide for reconstitution and delivery of a liquid injectable form of the medicament.

The apparatus may include, and the methods may involve, a stopper for a medicament delivery device. The delivery device may be cylindrical. The stopper may include a base for sealing an opening of the device. The base may include a central axis. The stopper may include a single elongated member. The stopper may include two or more elongated members. One or more of the elongated members may have a length. The length may be the same or different from lengths of other elongated members. The one or more elongated members may extend away from the base in a direction that is parallel to the axis. The member or members may be set radially away from the axis. The member or members may define: (1) a portion of a central well coaxial with the axis; and (2), extending in a circumferential direction between adjacent portions of a member or between adjacent members, a void. The void may be one of a plurality of voids. Each void of the plurality of voids may be similar.

The void may have a circumferential span. The span may be a portion of a circumference of the stopper. The circumference of the stopper may be a circumference of the base. A void, or a plurality of voids in aggregate, may span a portion of the circumference. The void portion may be referred to as a void-fraction circumference.

The stopper may have a first operational configuration. The stopper may have a second operational configuration.

In the first operational configuration, the elongated member or members may engage an inner wall of the device to support the base away from the opening such that the void provides exchange of gas between an interior and an exterior of the device.

In the second operational configuration, the base may engage the inner wall to seal the opening.

In the first operational configuration, the gas may be a lyophilization byproduct.

In the second operational configuration, the stopper may seal a lyophilized product within the device. The product may be disposed between the stopper and a plunger that is sealingly engaged with the inner wall of the device.

An operator may move the stopper from the first operational configuration to the second operational configuration by advancing the stopper relative to the opening. The operator may be human. The operator may be mechanical. The operator may be robotic. The operator may be any other suitable operator.

The base may adjoin a flange orthogonal to the axis. The base may include the flange. The flange may be configured to abut, in the second operational configuration, a terminal surface of the device. The terminal surface may surround the opening.

The stopper may include a resilient material. The stopper may include a lubricious coating. The lubricious coating may coat the resilient material. The lubricious coating may laminate the resilient material. The lubricious coating may be bonded to the resilient material. The resilient material may bear the lubricious coating.

The stopper may be manufactured by molding the resilient material and the lubricious coating in conjunction with each other. The molding may be accomplished through an overmolding process. The molding may be accomplished through a coinjection process.

The resilient material may include include rubber. The rubber may include chlorobutyl rubber. The rubber may include bromobutyl rubber. The rubber may include chromobutyl rubber. The resilient material may include silcone. The silicone may be molded as a liquid silicone rubber (LSR). The resilient material may include a thermoplastic elastomer. The resilient material may include a polymeric substance.

The lubricious coating may include polytetrafluoroethylene (PTFE). The lubricious coating may include ethylene tetrafluoroethylene (ETFE). The lubricious coating may include a material selected to reduce interaction of the coated surfaces with the medicament. The lubricious coating may confer chemical resistance and/or chemical inertness to coated surfaces. The lubricious coating may facilitate movement of the stopper into the delivery device. The lubricious coating may facilitate movement of the stopper within the delivery device. The lubricious coating may facilitate sealing engagement and/or sliding engagement of the stopper with the inner wall.

The base may include a region that is configured to be penetrated by a needle. The region may be self-sealing around an outer wall of the needle.

The central well may taper toward the base. The central well may taper continuously toward the base.

The base may include a peripheral ridge. The ridge may be configured to sealingly engage the inner wall of the device.

The device may include a tube. The tube may include glass. The tube may include rigid plastic. The tube may include any other suitable material.

The opening of the device may be an opening of the tube. The terminal surface of the device may be a terminal surface of the tube surrounding the opening of the tube. The inner wall of the device may be an inner wall of the tube. The interior of the device may be an interior of the tube surrounded by the inner wall of the tube. The exterior of the device may be an exterior of the tube.

The tube may be a part of a syringe. The tube may be part of a pre-filled syringe. The pre-filled syringe may be all or part of the device. The tube may be all or part of the device.

The tube may not be joined with other parts of the pre-filled syringe while the stopper is in the first operational configuration. The tube may be joined with other parts of the pre-filled syringe while the stopper is in the first operational configuration. The tube may be joined with other parts of the pre-filled syringe only when the stopper is in the second operational configuration.

In the first operational configuration, the lyophilization byproduct gas may be transferred from the interior of the device to the exterior of the device. The lyophilization byproduct may be exchanged for ambient air, initially exterior to the device (for example, air within a lyophilization chamber into which the device was placed), which may be transferred from the exterior of the device to the interior of the device.

In the second operational configuration, the stopper may be advanced into the device to sealingly engage the inner wall of the device and/or to abut the terminal surface of the device. The stopper sealingly engaging the inner wall of the device and/or abutting the terminal surface of the device may seal the lyophilized product within the device between the stopper and the plunger. The device may be joined with other parts of the pre-filled syringe while the stopper is in the second operational configuration.

The methods may include sealingly engaging the inner wall of the device with the plunger. A plunger face closest to the opening of the device may be offset from the opening. The methods may include orienting the device with the opening at least partly upright above the engaged plunger. The methods may include placing the medicament into the device. The methods may include placing the medicament into the device such that the medicament occupies at least part of the interior volume of the device above the plunger, below the opening and bound by the inner wall.

The methods may include engaging the inner wall of the device with a resilient elongated member fixed to a sealing base of the stopper or with a plurality of resilient elongated members fixed to the sealing base.

The methods may include advancing the member or members into the device until the base is set apart from the inner wall by a predetermined offset. The offset may be referred to as "S." The offset may scale in proportion to the void-fraction circumference. For example, the offset may range from about 1-5%, 6-10%, 11-15%, 16-20%, 21-25%, 26-30%, 31-35%, 36-40%, 41-45%, 46-50%, 51-55%, 56-60%, 61-65%, 66-70%, 71-75%, 76-80%, 81-85%, 86-90%, 91-95% or 96-99% of the void-fraction circumference.

The offset may scale in proportion to the length of the member or members. For example, the offset may range from about 1-5%, 6-10%, 11-15%, 16-20%, 21-25%, 26-30%, 31-35%, 36-40%, 41-45%, 46-50%, 51-55%, 56-60%, 61-65%, 66-70%, 71-75%, 76-80%, 81-85%, 86-90%, 91-95% or 96-99% of the length of the member or members.

The base may be held in place relative to the device by the member or members. The base may be held in place relative to the device only by the member or members.

The methods may include lyophilizing the medicament to produce a vapor. The vapor may escape between the inner wall, the member or members, and the base. The methods may include lyophilizing the medicament to produce an at least partly desiccated form of the medicament.

The methods may include advancing the member or members into the device until the base seals against the inner wall of the device. The methods may include advancing the member or members into the device until the base seals against the inner wall only after lyophilizing the medicament. The methods may include advancing the member or members into the device until the flange abuts the terminal surface of the device. The methods may include advancing the member or members into the device until the flange abuts the terminal surface only after lyophilizing the medicament.

The medicament may include a formulation of one or more compounds. The compounds may include naturally occurring substances. The compounds may include substances derived from naturally occurring substances. The compounds may include synthetically produced substances. The compounds may include chimeric substances. The compounds may include engineered substances. The compounds may include humanized substances. The compounds may include substances produced by recombinant techniques. The compounds may include substances modified by recombinant techniques.

The compounds may include a drug accepted for therapeutic treatment of a patient. The compounds may include a substance used in a therapeutic protocol. The compounds may include a substance used in a diagnostic protocol. The compounds may include a substance used in an experimental protocol. The compounds may include a substance compatible for use with apparatus and methods of the invention.

The medicament may include any medical agent listed herein, either alone or in combination with one or more other listed medical agents or with one or more other, non-listed, medical agents. The medical agents may include anti-glaucoma medications, other ocular agents, neuroprotective agents, antimicrobial agents, anti-inflammatory agents (including steroids and non-steroidal compounds), and biological agents including hormones, enzymes or enzyme-related components, antibodies or antibody-related components, oligonucleotides (including DNA, RNA, short-interfering RNA, and other suitable oligonucleotides, such as antisense oligonucleotides), DNA/RNA vectors, viruses or viral vectors, peptides, and proteins. The medical agents may include anti-angiogenesis agents, including angiostatin, anecortave acetate, thrombospondin, vascular endothelial growth factor (VEGF) receptor tyrosine kinase inhibitors, and anti-VEGF drugs, such as ranibizumab)(LUCENTIS®), bevacizumab (AVASTIN®), pegaptanib (MACUGEN®), sunitinib, and sorafenib, and any of a variety of known small-molecule and transcription inhibitors having an anti-angiogenesis effect; ophthalmic drugs, including glaucoma agents, such as adrenergic antagonists, including beta-blocker agents such as atenolol, propranolol, metipranolol, betaxolol, carteolol, levobetaxolol, levobunolol and timolol. The medical agents may include platelet-derived growth factor (PDGF) inhibitors and anti-PDGF drugs. The medical agents may include transformation growth factor (TGF) inhibitors and anti-TGF drugs. The medical agents may include anti-inflammatory agents including glucocorticoids and corticosteroids, such as betamethasone, cortisone, dexamethasone, dexamethasone 21-phosphate, methylprednisolone, prednisolone 21-phosphate, prednisolone acetate, prednisolone, loteprednol, medrysone, fluocinolone acetonide, triamcinolone acetonide, triamcinolone, beclomethasone, budesonide, flunisolide, fluorometholone, fluticasone, hydrocortisone, hydrocortisone acetate and rimexolone; and non-steroidal anti-inflammatory agents including diclofenac, flurbiprofen, ibuprofen, bromfenac, nepafenac, ketorolac, salicylate, indomethacin, naxopren, naproxen, piroxicam and nabumetone. The medical agents may include anti-cytokine agents; the medical agents may include anti-interleukin-6 agents such as tocilizumab (ACTEMRA®)). The medical agents may include anti-complement agents, including those targeting complement factor D (such as an anti-complement factor D antibody or an antigen-binding fragment thereof) such as lampalizumab, and those targeting complement factor H (such as an anti-complement factor H antibody or an antigen-binding fragment thereof). The medical agents may include angiopoietin-specific agents, such as an angiopoietin-2 antibody or an antigen-binding fragment thereof. The medical agents may include human growth hormone. The medical agents may include any suitable medical agent.

The medicament may include one or more derivatives of any of the above-mentioned medical agents. The medicament may include advanced forms of any of the above-mentioned medical agents. The medicament may include mutated forms of any of the above-mentioned medical agents. The medicament may include combinations of any of the above-mentioned medical agents. The combinations may be incorporated into a multi-specific molecule. The multi-specific molecule may exhibit properties of its constituent parts. The multi-specific molecule may exhibit properties different from any if its constituent parts. The medicament may include depots, hydrogels and pegylated forms of any of the above medical agents. The medicament may include any suitable form of any of the above medical agents.

Apparatus and methods in accordance with the invention will now be described in connection with the FIGS. The FIGS. show illustrative features of apparatus and methods in accordance with the principles of the invention. The features are illustrated in the context of selected embodiments. It will be understood that features shown in connection with one of the embodiments may be practiced in accordance with the principles of the invention along with features shown in connection with another of the embodiments.

Apparatus and methods of the invention may involve some or all of the features of the illustrative apparatus and/or some or all of the steps of the illustrative methods. The steps of the methods may be performed in an order other than the order shown and described herein. Some embodiments may omit steps shown and described in connection with the illustrative methods. Some embodiments may include steps that are not shown and described in connection with the illustrative methods.

Illustrative embodiments will now be described with reference to the accompanying drawings, which form a part hereof.

The apparatus and methods of the invention will be described in connection with embodiments and features of illustrative devices. The devices will be described now with reference to the FIGS. It is to be understood that other embodiments may be utilized and structural, functional and procedural modifications may be made without departing from the scope and spirit of the present invention.

Some FIGS. may indicate dimensions of apparatus features. Illustrative values of the indicated dimensions are presented below following description of all the FIGS.

FIG. 1 shows illustrative medicament delivery device 100. Delivery device 100 may include stopper 102. Delivery device 100 may include tube 104. Delivery device 100 may include medial plunger 106.

Delivery device 100 is shown in a first operational state.

Stopper 102 may include sealing base 108. Stopper 102 may include one or more elongated members 110. Elongated members 110 may define, in spaces circumferentially between elongated members 110, one or more voids 112. Stopper 102 may include flange 116.

Tube 104 may be cylindrical. Tube 104 may include distal opening 118. Tube 104 may include inner wall 120. Tube 104 may include terminal surface 122. Tube 104 may include one or more bypass channels 124.

Medial plunger 106 may sealingly engage inner wall 120. Medial plunger 106 may partition tube 104 into medicament chamber 126 and liquid chamber 128. Medicament chamber 126 may be proximally limited by medial plunger 106. Liquid chamber 128 may be distally limited by medial plunger 106. Liquid chamber 128 may be proximally limited by a proximal plunger (not shown).

In the first operational state, stopper 102 may be partially inserted into tube 104 through distal opening 118. Partial insertion of stopper 102 into tube 104 through distal opening 118 may engage elongated members 110 with inner wall 120. Engagement of elongated members 110 with inner wall 120 upon the partial insertion of stopper 102 may set sealing base 108 distally apart from distal opening 118. Sealing base 108 may be set distally apart from distal opening 118 by offset S.

Void 112 may be distally open to an exterior of tube 104 in a region of offset S. Void 112 may be proximally open to medicament chamber 126. Void 112 may provide gas exchange between medicament chamber 126 and the region of offset S. Gas exchange may be provided through an open-ended conduit (not depicted distinct from its components) that includes: (1) proximally and distally open void 112; (2) circumferentially adjacent elongated members 110 defining void 112 and engaging with inner wall 120 alongside void 112; and (3) a region of inner wall 120 circumferentially overlying void 112.

The first operational state may be utilized for lyophilization of a medicament (not shown) that has been placed in medicament chamber 126 prior to the partial insertion of stopper 102 into tube 104 through distal opening 118. During lyophilization, gas exchanged from medicament chamber 126 to the exterior of tube 104 via void 112 may be a lyophilization byproduct. The lyophilization byproduct may be vaporized medicament solvent (not shown). Lyophilization may continue until a lyophilized product (not shown) remains in medicament chamber 126. The lyophilized product may be a caked desiccated medicament.

Figure 2:
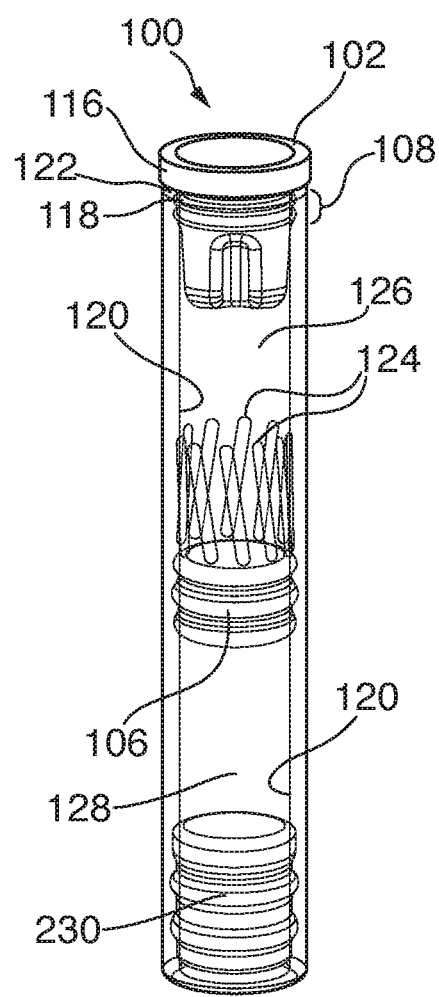
FIG. 2 is a perspective view of apparatus in accordance with the principles of the invention.

FIG. 2 shows medicament delivery device 100 in a second operational state.

Stopper 102 may be displaced relative to the configuration shown in FIG. 1 such that flange 116 abuts terminal surface 122. Flange 116 abutting terminal surface 122 may seal distal opening 118. Displacing stopper 102 such that flange 116 abuts terminal surface 122 may bring sealing base 108 into sealing engagement with inner wall 120. Sealing base 108 being brought into sealing engagement with inner wall 120 may distally seal medicament chamber 126.

The second operational state may be utilized for sealing the lyophilized product (not shown) in medicament chamber 126. The second operational state may be utilized for storing the lyophilized product in medicament chamber 126. The lyophilized product in medicament chamber 126 may be sealed between stopper 102 and medial plunger 106. Sealing the lyophilized product in medicament chamber 126 between stopper 102 and medial plunger 106 may contribute to long-term stability of the lyophilized product.

Proximal plunger 230 may sealingly engage inner wall 120. Liquid chamber 128 may be proximally limited by proximal plunger 230. Diluent (not shown) may be sealed in liquid chamber 128 between medial plunger 106 and proximal plunger 230.

The lyophilized product (not shown) may be reconstituted to a liquid injectable form of the medicament (not shown). The lyophilized product may be reconstituted with diluent (not shown) stored in liquid chamber 128. The diluent may be transferred from liquid chamber 128 to medicament chamber 126 through bypass channels 124.

In delivery device 100, transferring diluent to medicament chamber 126 through bypass channels 124 may involve advancing proximal plunger 230 distally within tube 104 toward medial plunger 106. Transferring diluent to medicament chamber 126 through bypass channels 124 may involve advancing medial plunger 106 distally within tube 104 toward stopper 102. Transferring diluent to medicament chamber 126 through bypass channels 124 may involve providing a vent (not shown) that passes through stopper 102 in the second operational state. A lumen of a needle (not shown) embedded in stopper 102 may provide the vent through stopper 102 in the second operational state, the lumen providing fluid communication between medicament chamber 126 and the exterior of tube 104. The needle may be timely inserted, prior to transferring the diluent, through septum region 611 (shown in FIG. 6a) of sealed delivery device 100. The needle may serve to deliver to a patient (not shown) the liquid injectable form of the medicament reconstituted from the lyophilized product.

Figure 3:
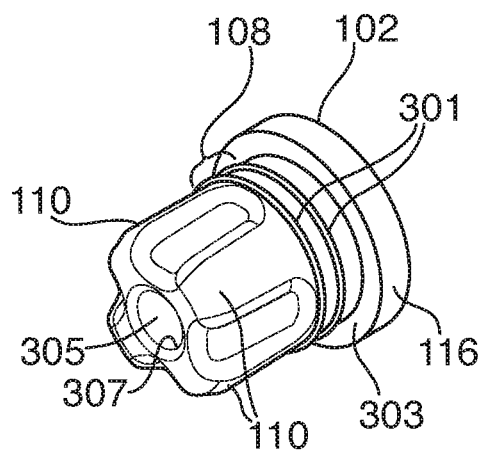
FIG. 3 is a perspective view of apparatus in accordance with the principles of the invention.

FIG. 3 shows stopper 102. Stopper 102 may include one or more peripheral sealing ridges 301. Peripheral sealing ridges 301 may be integral to sealing base 108. Peripheral sealing ridges 301 may facilitate sealing engagement of sealing base 108 with inner wall 120 (shown in FIG. 2).

Stopper 102 may include sealing ledge 303. Sealing ledge 303 may be integral to flange 116. Sealing ledge 303 may extend radially inward from a circumferential periphery of flange 116. At an innermost radial extension, sealing ledge 303 may form a circumferential juncture of flange 116 and sealing base 108. Sealing ledge 303 may facilitate sealing of distal opening 118 (shown in FIG. 2) when flange 116 abuts terminal surface 122 (shown in FIG. 2).

Stopper 102 may include central well 305. Central well 305 may be at least partly defined by elongated members 110. Elongated members 110 may partly define central well 305 by merging into webbing surface 307 interior to stopper 102. Central well 305 may extend interior to the stopper towards sealing base 108.

Figure 4A:
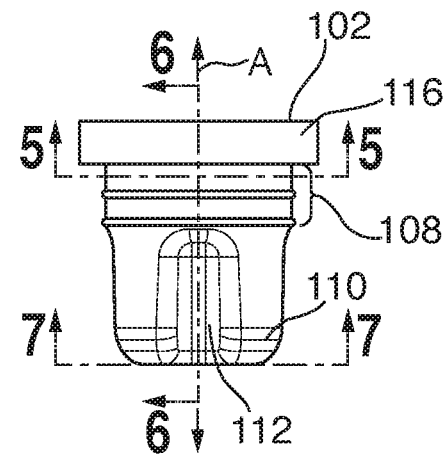
FIG. 4a is another perspective view of the apparatus shown in FIG. 3.

FIG. 4a shows stopper 102, including sealing base 108, elongated members 110, void 112 and flange 116. (FIG. 4a indicates viewlines associated with sealing base 108, elongated members 110, void 112 and flange 116.) Stopper 102 may define longitudinal axis A. Longitudinal axis A may pass through base 108. Longitudinal axis A may be coaxial with a central axis of base 108 (not shown).

Figure 4B:
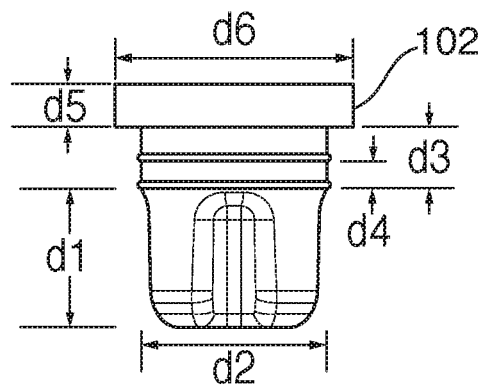

FIG. 4b shows stopper 102, in the same view as shown in FIG. 4a, with associated illustrative dimensions d1, d2, d3, d4, d5 and d6 indicated.

Figure 5:
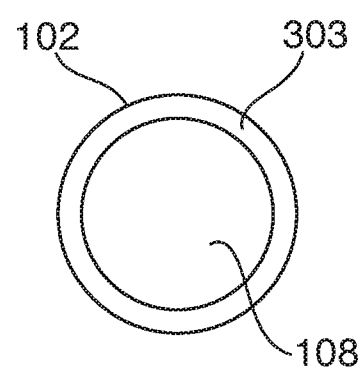
FIG. 5 is a partial cross-sectional view of the apparatus shown in FIG. 3, the view taken along lines 5-5 (shown in FIG. 4a)

FIG. 5 shows stopper 102 in a cross-sectional view taken along lines 5-5 (through sealing base 108, as shown in FIG. 4a). FIG. 5 shows sealing ledge 303 surrounding sealing base 108.

Figure 6A:
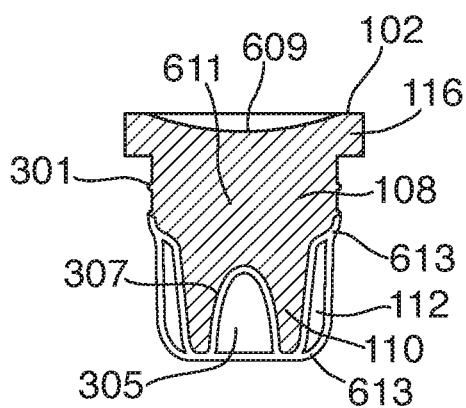
FIG. 6a is a partial cross-sectional view of the apparatus shown in FIG. 3, the view taken along lines 6-6 (shown in FIG. 4a)

FIG. 6a shows stopper 102 in a cross-sectional view taken along lines 6-6 (through flange 116, sealing base 108 and void 112, as shown in FIG. 4a). FIG. 6a shows septum surface 609 associated with flange 116. Septum surface 609 may be an outer surface of septum region 611. Septum region 611 may extend through flange 116 and sealing base 108. Septum region 611 may extend between septum surface 609 and central well 305. Septum region 611 may be a self-sealing needle-penetrable region, allowing a needle to be inserted, and then extend with its outer wall sealed, from the exterior of medicament delivery device 100 (shown in FIG. 2) into central well 305.

Lubricious coating 613 may coat surfaces of stopper 102. Lubricious coating 613 may be bonded to coated surfaces. Lubricious coating 613 may coat surfaces of elongated members 110 and void 112. Lubricious coating 613 may coat webbing surface 307. Surfaces of stopper 102 may not bear lubricious coating 613. Surfaces of stopper 102 that serve to sealingly engage inner wall 120 (shown in FIG. 2), such as peripheral sealing ridges 301, may not be coated with lubricious coating 613. Surfaces of peripheral sealing ridges 301 may be selectively coated with lubricious coating 613. All or part of the surfaces of none, one or more than one of peripheral sealing ridges 301 may be coated with lubricious coating 613.

Figure 6B:
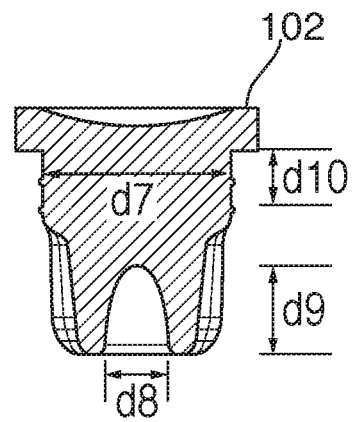
FIG. 6b is another partial cross-sectional view of the apparatus shown in FIG. 3, the view taken along lines 6-6 (shown in FIG. 4a)

FIG. 6b shows stopper 102, in the same view as shown in FIG. 6a, with associated illustrative dimensions d7, d8, d9 and d10 indicated.

Figure 7:
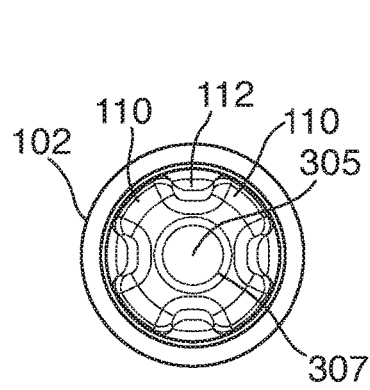
FIG. 7 is an end-view of the apparatus shown in FIG. 3, the view taken along lines 7-7 (shown in FIG. 4a)

FIG. 7 shows stopper 102 in end-view taken along lines 7-7 (along aspects of elongated members 110 and void 112, as shown in FIG. 4a). FIG. 7 shows circumferentially adjacent elongated members 110 defining between them void 112. Adjacent surfaces of elongated members 110 that are on the exterior of stopper 102 may merge to define void 112. Adjacent surfaces of elongated members 110 that are interior to stopper 102 may merge to form part of webbing surface 307 of central well 305.

Figure 8:
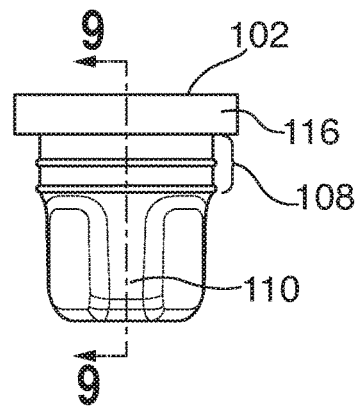
FIG. 8 is another perspective view of the apparatus shown in FIG. 3.

FIG. 8 shows stopper 102 rotated about longitudinal axis A (shown in FIG. 4a) relative to the view of stopper 102 shown in FIG. 4a. The rotation may be a rotation of about 45°. FIG. 8 shows sealing base 108, elongated members 110 and flange 116. (FIG. 8 indicates a viewline through stopper 102, the viewline associated with flange 116, sealing base 108 and elongated member 110.)

Figure 9:
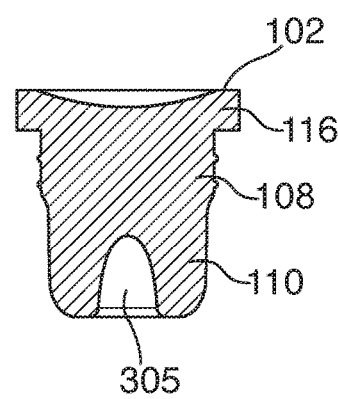
FIG. 9 is a partial cross-sectional view of the apparatus shown in FIG. 3, the view taken along lines 9-9 (shown in FIG. 8)

FIG. 9 shows stopper 102 in a cross-sectional view taken along lines 9-9 (through flange 116, sealing base 108 and elongated member 110, as shown in FIG. 8). FIG. 9 shows sealing base 108, elongated members 110, flange 116 and central well 305.

Figure 10A:
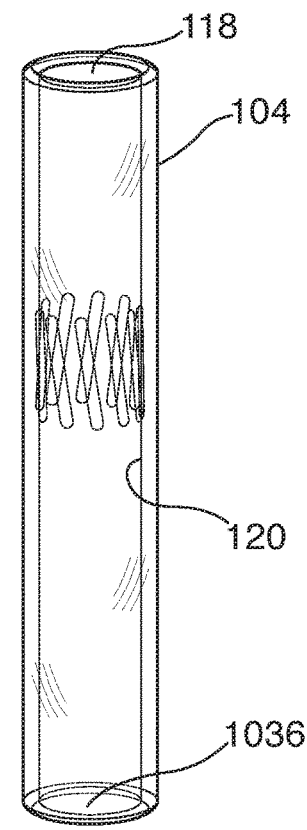
FIG. 10a is a perspective view of apparatus in accordance with the principles of the invention.

FIG. 10a shows tube 104. Tube 104 may include proximal opening 1036. Proximal opening 1036 may be opposite distal opening 118. Proximal opening 1036 may be parallel to distal opening 118. Inner wall 120 may extend between proximal opening 1036 and distal opening 118. Inner wall 120 may extend from proximal opening 1036 to distal opening 118.

Figure 10B:
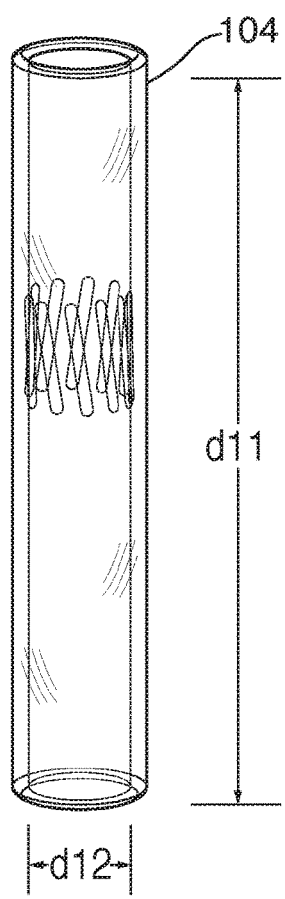
FIG. 10b is another perspective view of apparatus in accordance with the principles of the invention.

FIG. 10b shows tube 104, in the same view as shown in FIG. 10a, with associated illustrative dimensions d11 and d12 indicated.

Figure 11:
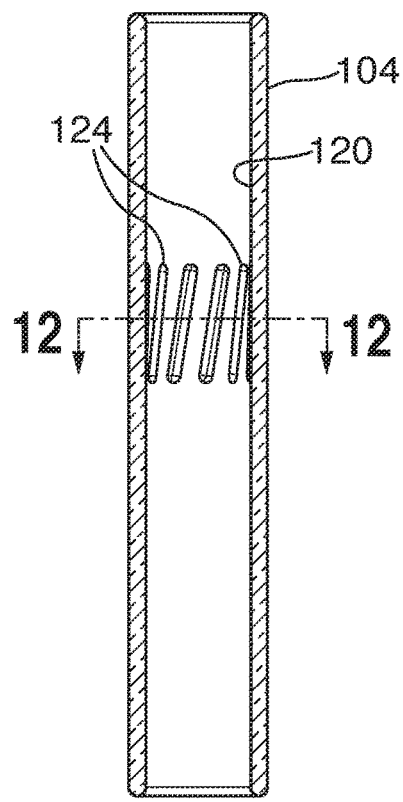

FIG. 11 shows a cross-sectional view of tube 104. FIG. 11 shows inner wall 120 and bypass channels 124. (FIG. indicates a viewline through tube 104, the viewline associated with inner wall 120 and bypass channels 124.)

Figure 12:
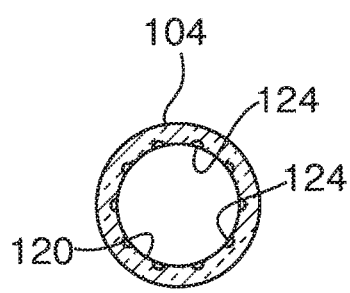
FIG. 12 is a partial cross-sectional view of the apparatus shown in FIG. 10a, the view taken along lines 12-12 (shown in FIG. 11)

FIG. 12 shows tube 104 in cross-sectional view taken along lines 12-12 (passing through inner wall 120 and bypass channels 124, as shown in FIG. 11). FIG. 12 shows tube 104, inner wall 120 and bypass channels 124.

Figure 13:
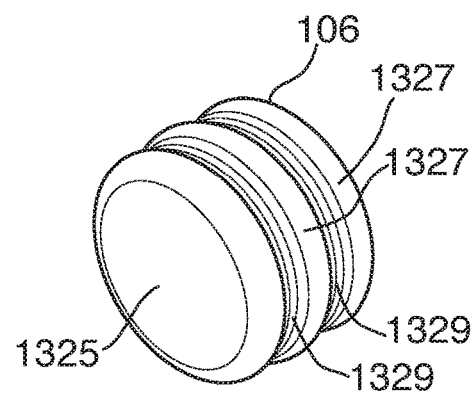
FIG. 13 is a perspective view of apparatus in accordance with the principles of the invention.

FIG. 13 shows medial plunger 106. Medial stopper 106 may include medial plunger face 1325. Medial stopper 106 may include two or more medial plunger side crests 1327. Medial plunger side crests 1327 may be of different girths parallel to medial plunger face 1325. Differently girthed medial plunger side crests 1327 may facilitate sealing engagement of medial plunger 106 with inner wall 120 (shown in FIG. 1). Differently girthed medial plunger side crests 1327 may facilitate sliding engagement of medial plunger 106 along inner wall 120 (shown in FIG. 1). Medial plunger 106 may include medial plunger side troughs 1329.

Figure 14A:
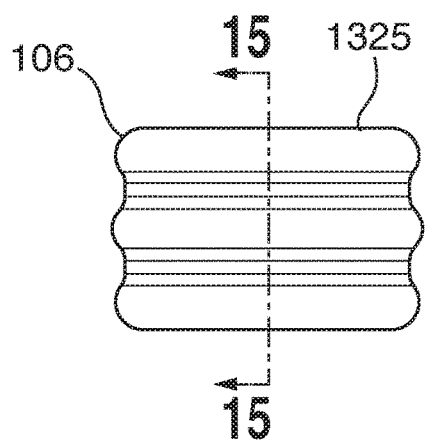
FIG. 14a is another perspective view of the apparatus shown in FIG. 13.

FIG. 14a shows a side view of medial plunger 106, including medial plunger face 1325. (FIG. 14a indicates a viewline through medial plunger 106, the viewline associated with medial plunger face 1325.)

Figure 14B:
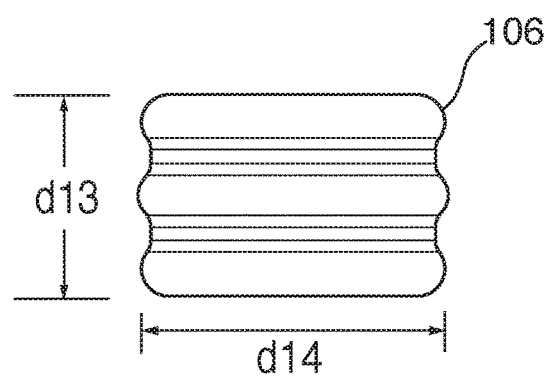

FIG. 14b shows medial plunger 106, in the same view as shown in FIG. 14a, with associated illustrative dimensions d13 and d14 indicated.

Figure 15A:
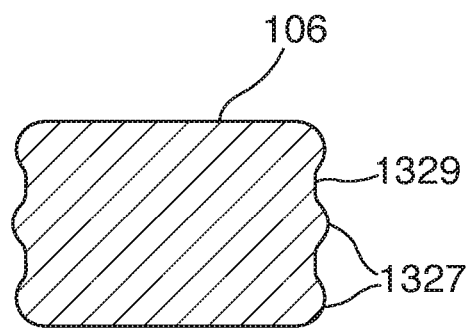
FIG. 15a is a cross-sectional view of the apparatus shown in FIG. 13, the view taken along lines 15-15 (shown in FIG. 14a)

FIG. 15a shows medial plunger 106 in a cross-sectional view taken along lines 15-15 (passing through medial plunger face 1325, as shown in FIG. 14a). FIG. 15a shows medial plunger side crests 1327 and medial plunger side trough 1329.

Figure 15B:
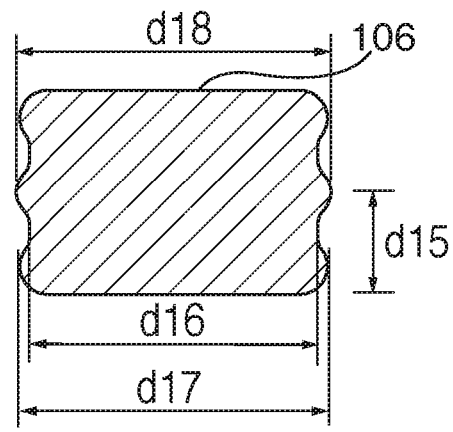
FIG. 15b is another cross-sectional view of the apparatus shown in FIG. 13, the view taken along lines 15-15 (shown in FIG. 14a)

FIG. 15b shows medial plunger 106, in the same view as shown in FIG. 15a, with associated illustrative dimensions d15, d16, d17 and d18 indicated.

Figure 16:
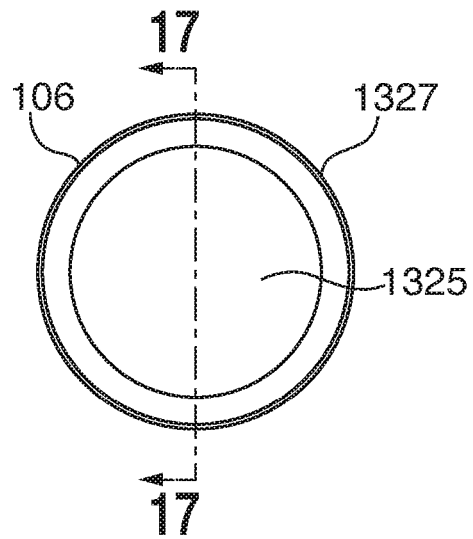
FIG. 16 is another perspective view of the apparatus shown in FIG. 13.

FIG. 16 shows medial plunger 106 viewed face-on. FIG. 16 shows medial plunger face 1325 and medial plunger side crest 1327. (FIG. 16 indicates a viewline through medial plunger 106, the viewline associated with medial plunger face 1325 and medial plunger side crest 1327.)

Figure 17:
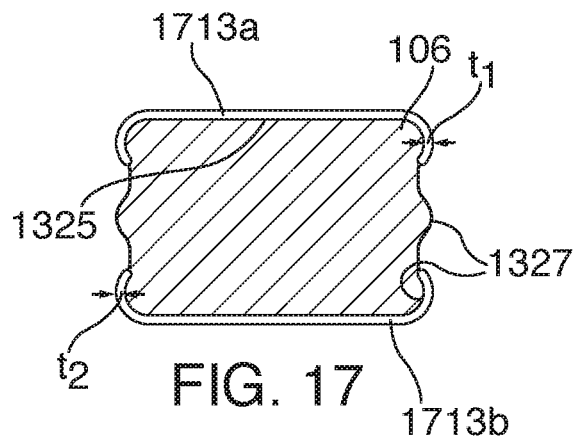
FIG. 17 is a cross-sectional view of the apparatus shown in FIG. 13, the view taken along lines 17-17 (shown in FIG. 16)

FIG. 17 shows medial plunger 106 in a face-up cross-sectional view taken along lines 17-17 (passing through medial plunger face 1325 and medial plunger side crest 1327, as shown in FIG. 16). FIG. 17 shows medial plunger face 1325 bearing lubricious coating 1713a. FIG. 17 shows a face of medial plunger 106 opposite medial plunger face 1325 bearing lubricious coating 1713b. Lubricious coating 1713b may include the same material as lubricious coating 1713a. Lubricious coating 1713b may not include the same material as lubricious coating 1713a. That material may be the same as the material included in lubricious coating 613 (shown in FIG. 6a).

Lubricious coating 1713a or lubricious coating 1713b may coat medial plunger side crests 1327. Lubricious coating 1713a may selectively coat none, one or more than one of medial plunger side crests 1327. None, one or more than one of medial plunger side crests 1327 may not bear lubricious coating 1713a or lubricious coating 1713b. Thickness t1 of lubricious coating 1713a or thickness t2 of lubricious coating 1713b may approximate differences of girth among medial plunger side crests 1327. Uncoated medial plunger side crests 1327 may be greater in girth than coated medial plunger side crests 1327, the difference approximated by thickness t1 or thickness t2. Coated medial plunger side crests 1327 may facilitate sliding engagement along inner wall 120 (shown in FIG. 2). Uncoated medial plunger side crests 1327 may facilitate sealing engagement with inner wall 120 (shown in FIG. 2).

Figure 18:
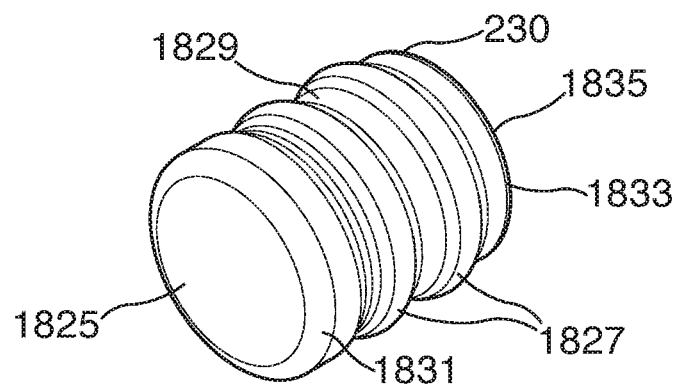
FIG. 18 is a perspective view of apparatus in accordance with the principles of the invention.

FIG. 18 shows proximal plunger 230. Proximal plunger 230 may include distal face 1825. Proximal plunger 230 may include proximal plunger side crests 1827. Proximal plunger 230 may include proximal plunger side trough 1829. Proximal plunger 230 may include leading edge 1831. Proximal plunger 230 may include trailing edge 1833. Proximal stopper 200 may include proximal face 1835.

A distal-to-proximal orientation of proximal plunger 230 within tube 104 (shown in FIGS. 2 and 10a) during engagement of proximal plunger 230 with inner wall 120 (as shown in FIG. 2) may be parallel to a distal-to-proximal alignment of distal opening 118 to proximal opening 1036 (both openings shown in FIG. 10a). Leading edge 1831 may be closer than trailing edge 1833 to distal opening 118 (shown in FIGS. 2 and 10a). Distal face 1825 may be closer than proximal face 1835 to distal opening 118 (shown in FIGS. 2 and 10a). Trailing edge 1833 may be closer than leading edge 1831 to proximal opening 1036 (shown in FIG. 10a). Proximal face 1835 may be closer than distal face 1825 to proximal opening 1036 (shown in FIG. 10a). A distal end of a practitioner-controlled syringe plunger rod (not shown) may act on proximal face 1835 to advance proximal plunger 230 distally within tube 104 (shown in FIG. 2).

Figure 19A:
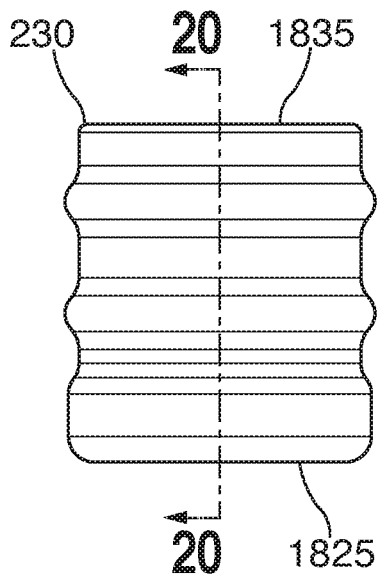
FIG. 19a is another perspective view of the apparatus shown in FIG. 18.

FIG. 19a shows a side view of proximal plunger 230, including distal face 1825 and proximal face 1835. (FIG. 19a indicates a viewline through proximal plunger 230, the viewline associated with distal face 1825 and proximal face 1835.)

Figure 19B:
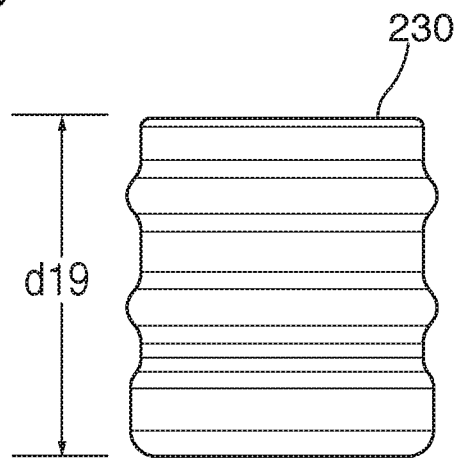
FIG. 19b is another perspective view of the apparatus shown in FIG. 18.

FIG. 19b shows proximal plunger 230, in the same view as shown in FIG. 19a, with associated illustrative dimension d19 indicated.

Figure 20A:
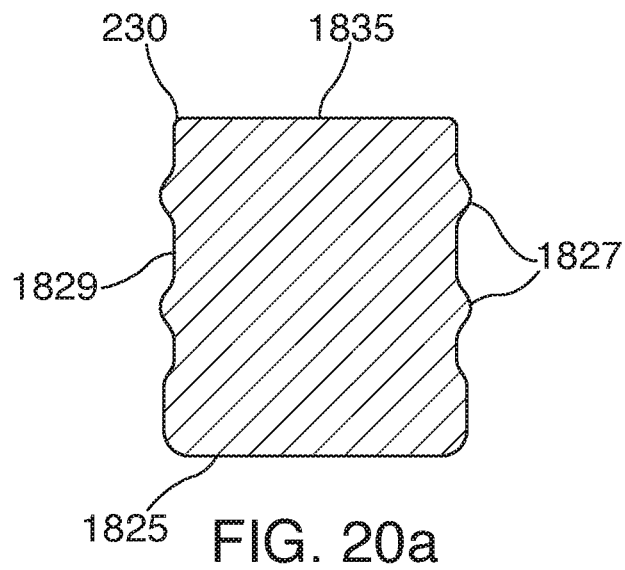
FIG. 20a is a cross-sectional view of the apparatus shown in FIG. 18, the view taken along lines 20-20 (shown in FIG. 19a)

FIG. 20a shows proximal plunger 230 in a cross-sectional view taken along lines 20-20 (passing through distal face 1825 and proximal face 1835, as shown in FIG. 19a). FIG. 20a shows distal face 1825, medial plunger side crests 1827, medial plunger side trough 1829 and proximal face 1835.

Figure 20B:
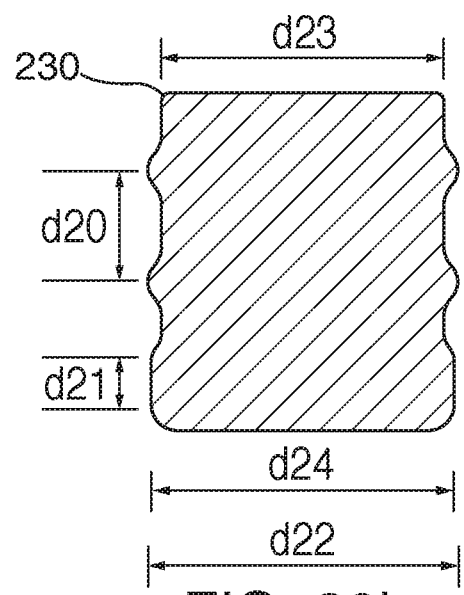
FIG. 20b is another cross-sectional view of the apparatus shown in FIG. 18, the view taken along lines 20-20 (shown in FIG. 19a)

FIG. 20b shows proximal plunger 230, in the same view as shown in FIG. 20a, with associated illustrative dimensions d20, d21, d22, d23 and d24 indicated.

Figure 21:
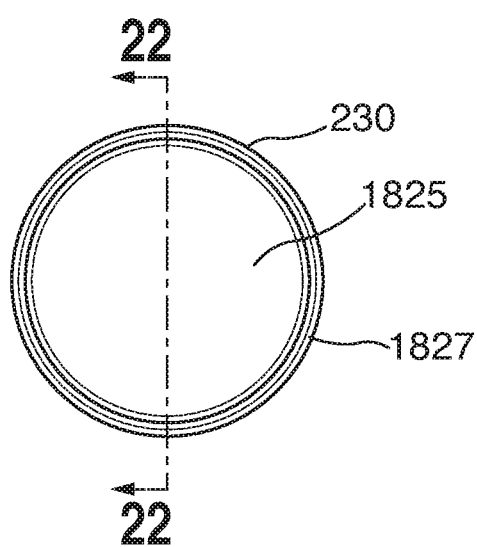
FIG. 21 is another perspective view of the apparatus shown in FIG. 18.

FIG. 21 shows proximal plunger 230 viewed face-on. FIG. 21 shows distal face 1825 and proximal plunger side crest 1827. (FIG. 21 indicates a viewline through proximal plunger 230, the viewline associated with distal face 1825 and proximal plunger side crest 1827.)

Figure 22:
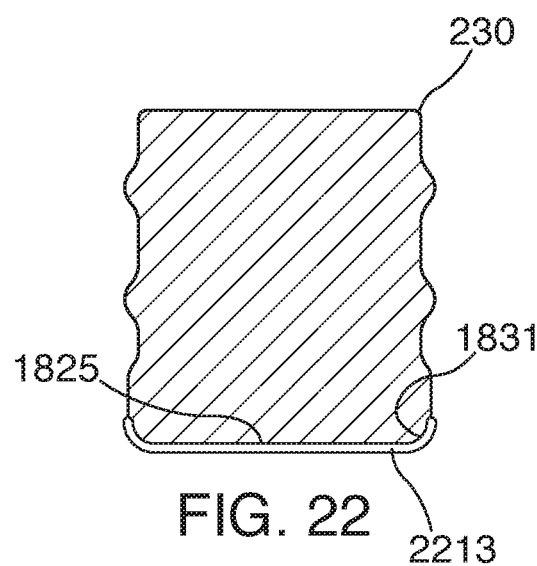
FIG. 22 is a cross-sectional view of the apparatus shown in FIG. 18, the view taken along lines 22-22 (shown in FIG. 21)

FIG. 22 shows proximal plunger 230 in a face-down cross-sectional view taken along lines 22-22 (passing through distal face 1825 and proximal plunger side crest 1827, as shown in FIG. 21). FIG. 22 shows medial plunger face 1825 bearing lubricious coating 2213. Medial plunger face 1825 may be selectively coated with lubricious coating 2213. None, some or all of a surface of medial plunger face 1825 may be coated with lubricious coating 2213. FIG. 22 shows leading edge 1831 bearing lubricious coating 2213. Leading edge 1831 may be selectively coated with lubricious coating 2213. None, some or all of a surface of leading edge 1831 may be coated with lubricious coating 2213. Lubricious coating 2213 may include the same material as lubricious coating 1713a or lubricious coating 1713b (both shown in FIG. 17).

Figure 23:
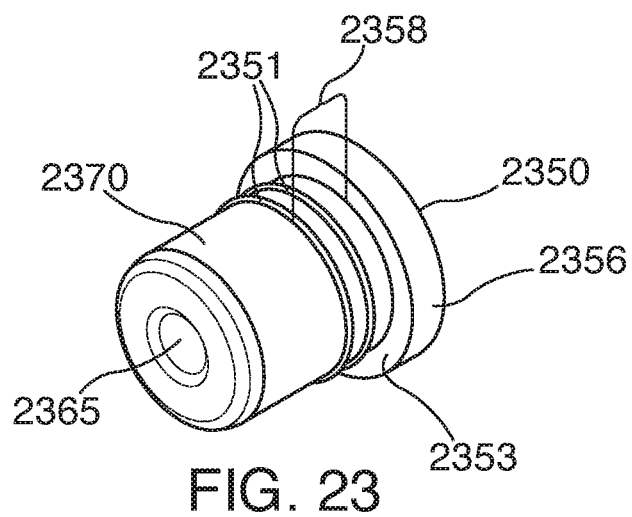
FIG. 23 is a perspective view of apparatus in accordance with the principles of the invention.

FIG. 23 shows unvented stopper 2350. Unvented stopper 2350 may have no, one or more than one features in common with stopper 102 (shown in FIG. 3). Unvented stopper 2350 may include one or more peripheral sealing ridges 2351. Peripheral sealing ridges 2351 may be integral to sealing base 2358. Unvented stopper 2350 may include sealing ledge 2353. Sealing ledge 2353 may be integral with flange 2356. Sealing ledge 2353 may extend radially inward from a circumferential periphery of flange 2356. At an innermost radial extension, sealing ledge 2353 may form a circumferential juncture of flange 2356 and sealing base 2358. Unvented stopper 2350 may include central well 2365 internal to elongated section 2370.

Figure 24A:
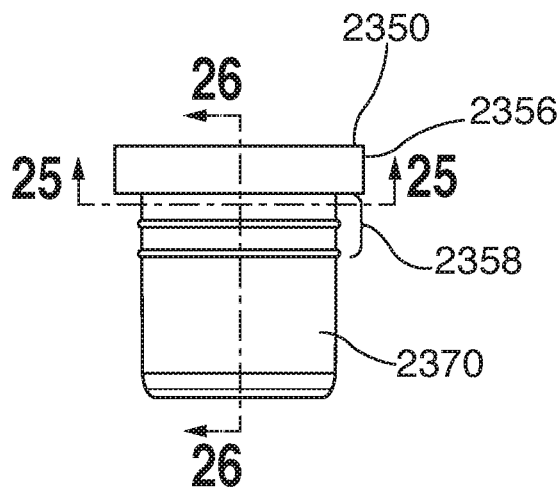
FIG. 24a is another perspective view of the apparatus shown in FIG. 23.

FIG. 24a shows unvented stopper 2350, including flange 2356, sealing base 2358 and elongated section 2370. (FIG. 24a indicates viewlines through unvented stopper 2350, the viewlines associated with flange 2356, sealing base 2358 and elongated section 2370.)

Figure 24B:
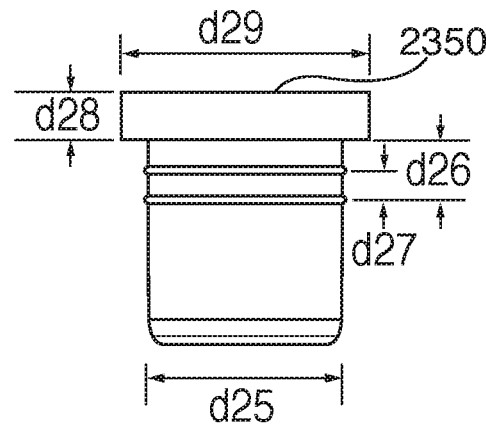
FIG. 24b is another perspective view of the apparatus shown in FIG. 23.

FIG. 24b shows unvented stopper 2350, in the same view as shown in FIG. 24a, with associated illustrative dimensions d25, d26, d27, d28 and d29 indicated.

Figure 25:
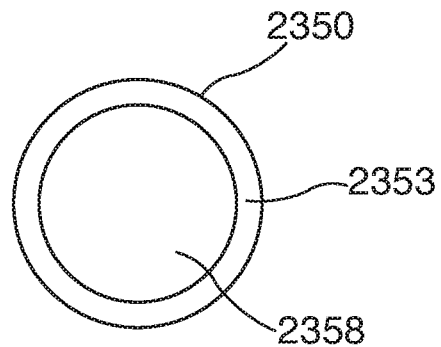
FIG. 25 is a partial cross-sectional view of the apparatus shown in FIG. 23, the view taken along lines 25-25 (shown in FIG. 24a)

FIG. 25 shows unvented stopper 2350 in a cross-sectional view taken along lines 25-25 (through sealing base 2358, as shown in FIG. 24a). FIG. 25 shows sealing ledge 2353 surrounding sealing base 2358.

Figure 26A:
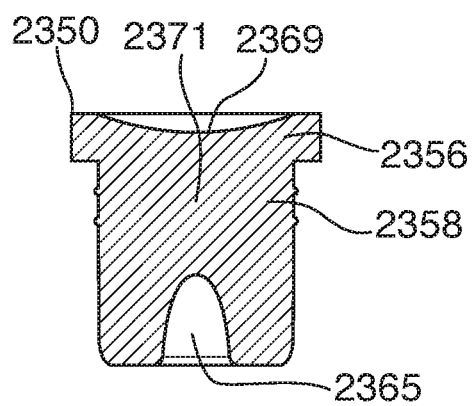
FIG. 26a is a partial cross-sectional view of the apparatus shown in FIG. 23, the view taken along lines 26-26 (shown in FIG. 24a)

FIG. 26a shows unvented stopper 2350 in a cross-sectional view taken along lines 26-26 (through flange 2356, sealing base 2358 and elongated section 2370, as shown in FIG. 24a). FIG. 26a shows septum surface 2369 associated with flange 2356. Septum surface 2369 may be an outer surface of septum region 2371. Septum region 2371 may extend through flange 2356 and sealing base 2358. Septum region 2371 may extend between septum surface 2369 and central well 2365. Septum region 2371 may be a self-sealing needle-penetrable region.

Figure 26B:
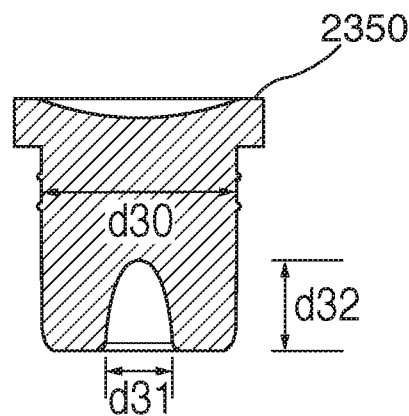
FIG. 26b is another partial cross-sectional view of the apparatus shown in FIG. 23, the view taken along lines 26-26 (shown in FIG. 24a)

FIG. 26b shows unvented stopper 2350, in the same view as shown in FIG. 26a, with associated illustrative dimensions d30, d31 and d32 indicated.

Figure 27:
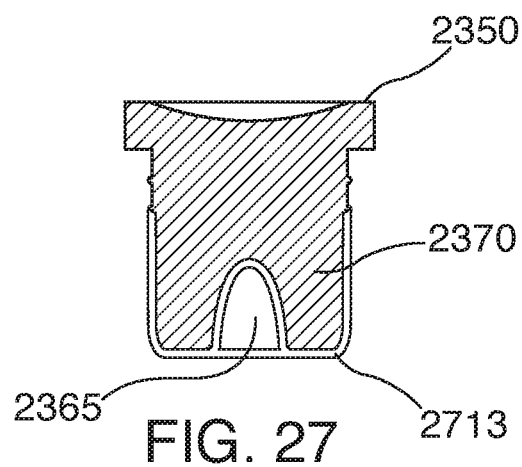
FIG. 27 is another partial cross-sectional view of the apparatus shown in FIG. 23, the view taken along lines 26-26 (shown in FIG. 24a)

FIG. 27 shows unvented stopper 2350 in a cross-sectional view similar to the view shown in FIG. 26a. FIG. 27 shows lubricious coating 2713 coating surfaces of unvented stopper 2350. Surfaces of unvented stopper 2350 may not bear lubricious coating 2713. Lubricious coating 2713 may selectively coat surfaces of elongated section 2370. None, some or all of a surface of elongated section 2370 may be coated with lubricious coating 2713. Lubricious coating 2713 may selectively coat surfaces of central well 2365. None, some or all of a surface of central well 2365 may be coated with lubricious coating 2713. Lubricious coating 2713 may include material of lubricious coating 2213 (shown in FIG. 22).

Figure 28:
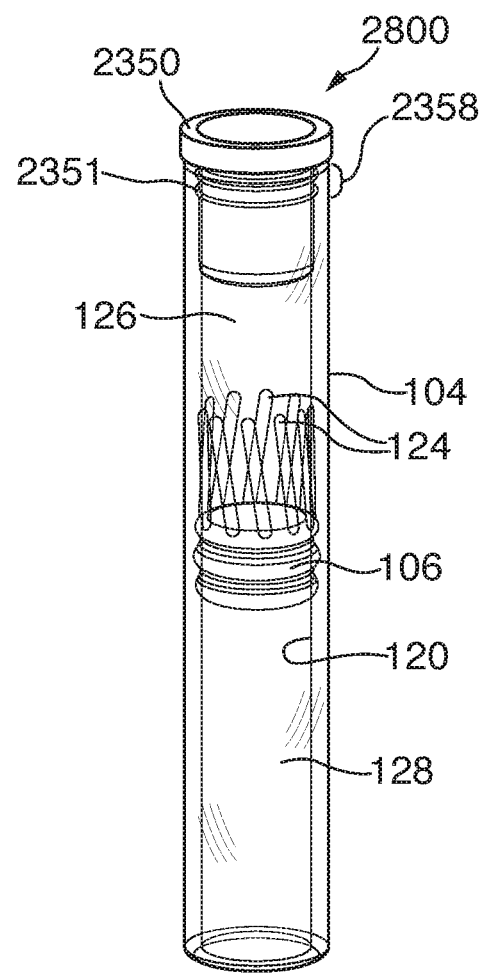
FIG. 28 is a perspective view of apparatus in accordance with the principles of the invention.

FIG. 28 shows illustrative medicament delivery device 2800. Delivery device 2800 may include tube 104, including inner wall 120 and bypass channels 124. Delivery device 2800 may include medial plunger 106 sealingly engaging inner wall 120 and partitioning tube 104 into medicament chamber 126 and liquid chamber 128.

Delivery device 2800 may include unvented stopper 2350. Unvented stopper 2350 is shown inserted into tube 104. Unvented stopper 2350 may seal tube 104. Sealing base 2358 of unvented stopper 2350 may sealingly engage inner wall 120. Sealing ridge 2351 may facilitate sealing engagement of unvented stopper 2350 with inner wall 120. Sealing engagement of unvented stopper 2350 with inner wall 120 and of medial plunger 106 with inner wall 120 may seal a medicament (not shown) within medicament chamber 126. The medicament within medicament chamber 126 of delivery device 2800 may be in a liquid state.

Figure 29:
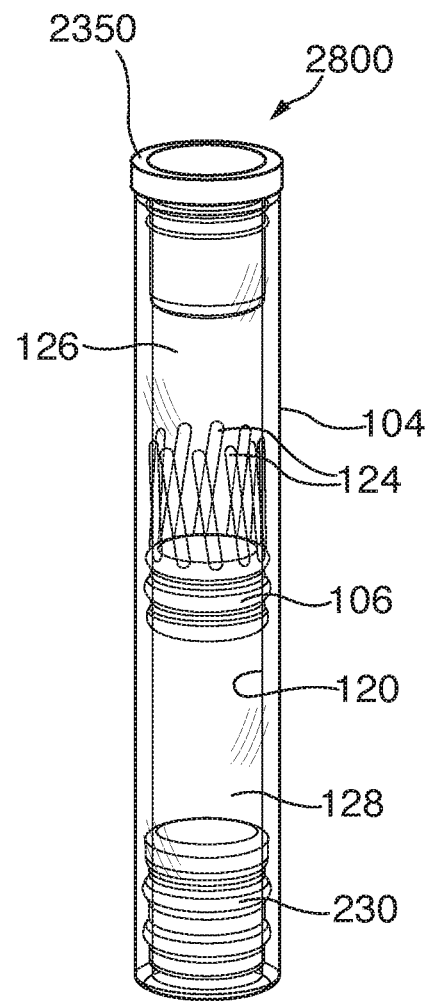
FIG. 29 is a perspective view of apparatus in accordance with the principles of the invention.

FIG. 29 shows medicament delivery device 2800 with liquid chamber 128 limited on opposing ends by medial plunger 106 and by proximal plunger 230, each plunger sealingly engaging inner wall 120. Sealing engagement of medial plunger 106 with inner wall 120 and of proximal plunger 230 with inner wall 120 may seal a fluid (not shown) within liquid chamber 128. The fluid may be transferred from liquid chamber 128 to medicament chamber 126 through bypass channels 124.

In delivery device 2800, transferring fluid to medicament chamber 126 through bypass channels 124 may involve advancing proximal plunger 230 distally within tube 104 toward medial plunger 106. Transferring fluid to medicament chamber 126 through bypass channels 124 may involve advancing medial plunger 106 distally within tube 104 toward unvented stopper 2350. Transferring fluid to medicament chamber 126 through bypass channels 124 may involve providing a vent (not shown) that passes through unvented stopper 2350. A lumen of a needle (not shown) embedded in unvented stopper 2350 may provide the vent through unvented stopper 2350, the lumen providing fluid communication between medicament chamber 126 and an exterior of tube 104. The needle may be timely inserted, prior to transferring the fluid, through septum region 2371 (shown in FIG. 26a) of sealed delivery device 2800.

Transferring fluid to medicament chamber 126 through bypass channels 124 may facilitate interaction of the fluid with the medicament (not shown) in medicament chamber 126. The interaction may involve mixing. The interaction may involve dilution. The interaction may involve reconstitution. The interaction may involve one or more chemical reactions. The interaction may convert a storage form of the medicament (not shown) stored between medial plunger 106 and unvented stopper 2350 into a deliverable form of the medicament. The deliverable form of the medicament may be delivered to a patient (not shown) via the needle (not shown) embedded in unvented stopper 2350.

Figure 30A:
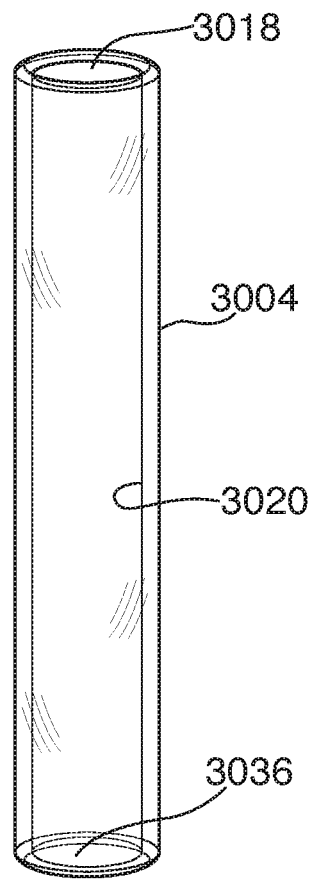
FIG. 30a is a perspective view of apparatus in accordance with the principles of the invention.

FIG. 30a shows tube 3004. Tube 3004 may have no, one or more than one features in common with tube 104 (shown in FIG. 10a). Tube 3004 may include distal opening 3018. Tube 3004 may include inner wall 3020. Tube 3004 may include proximal opening 3036. Proximal opening 3036 may be opposite distal opening 3018. Proximal opening 3036 may be parallel to distal opening 3018. Inner wall 3020 may extend between proximal opening 3036 and distal opening 3018. Inner wall 3020 may extend from proximal opening 3036 to distal opening 3018.

Figure 30B:
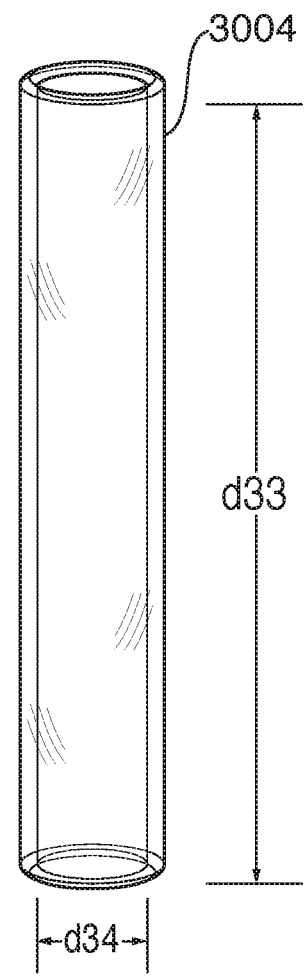

FIG. 30b shows tube 3004, in the same view as shown in FIG. 30a, with associated illustrative dimensions d33 and d34 indicated.

Figure 31:
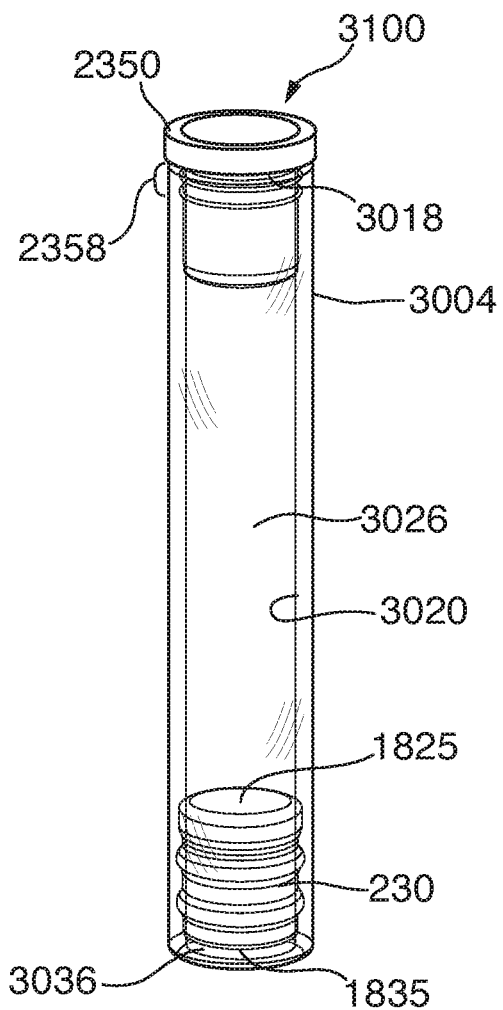
FIG. 31 is a perspective view of apparatus in accordance with the principles of the invention.

FIG. 31 shows illustrative medicament delivery device 3100. Delivery device 3100 may include tube 3004. Delivery device 3100 may include unvented stopper 2350. Unvented stopper 2350 may seal distal opening 3018. Sealing base 2358 may sealingly engage inner wall 3020 proximal to distal opening 3018. Delivery device 3100 may include proximal plunger 230. Proximal plunger 230 may sealingly engage inner wall 3020 distal to proximal opening 3036.

Unvented stopper 2350 and proximal plunger 230 may seal a medicament (not shown) within medicament chamber 3026. Medicament chamber 3026 may be limited proximally by distal face 1825. Medicament chamber 3026 may be limited distally by proximal features of unvented stopper 2350.

The medicament (not shown) within medicament chamber 3026 may be in a liquid state. The medicament within medicament chamber 3026 may be a deliverable form of the medicament.

A distal end of a practitioner-controlled syringe plunger rod (not shown) may act on proximal face 1835 to advance proximal plunger 230 distally within tube 3004. A lumen of a needle (not shown) embedded in unvented stopper 2350 may provide a vent through unvented stopper 2350, the lumen providing fluid communication between medicament chamber 3026 and the exterior of tube 3004. The needle may be timely inserted, prior to medicament delivery, through septum region 2371 (shown in FIG. 26a) of sealed delivery device 3100. The needle may serve to deliver the medicament to a patient (not shown).

Table 1 shows illustrative dimensions, in millimeters, of dimensions $d_i$ shown in, and referenced to, FIGS. 4b, 6b, 10b, 14b, 15b, 19b, 20b, 24b, 26b and 30b.

TABLE 1

Illustrative dimensions of $d_i$.

| $d_i$ | Value (mm) | FIG. in which $d_i$ is shown |
|---|---|---|
| d1 | 4.75 | FIG. 4b |
| d2 | 6.40 | FIG. 4b |
| d3 | 2 | FIG. 4b |
| d4 | 1 | FIG. 4b |
| d5 | 1.5 | FIG. 4b |
| d6 | 8.20 | FIG. 4b |
| d7 | 6.60 | FIG. 6b |
| d8 | 2.20 | FIG. 6b |

TABLE 1-continued

Illustrative dimensions of $d_i$.

| $d_i$ | Value (mm) | FIG. in which $d_i$ is shown |
|---|---|---|
| d9 | 3 | FIG. 6b |
| d10 | 2 | FIG. 6b |
| d11 | 39-54 | FIG. 10b |
| d12 | 6 | FIG. 10b |
| d13 | 4.5 | FIG. 14b |
| d14 | 6.75 | FIG. 14b |
| d15 | 2.25 | FIG. 15b |
| d16 | 6.30 | FIG. 15b |
| d17 | 6.75 | FIG. 15b |
| d18 | 6.90 | FIG. 15b |
| d19 | 7.5 | FIG. 19b |
| d20 | 2.50 | FIG. 20b |
| d21 | 0.90 | FIG. 20b |
| d22 | 6.90 | FIG. 20b |
| d23 | 6.30 | FIG. 20b |
| d24 | 6.75 | FIG. 20b |
| d25 | 6.40 | FIG. 24b |
| d26 | 2 | FIG. 24b |
| d27 | 1 | FIG. 24b |
| d28 | 1.50 | FIG. 24b |
| d29 | 8.20 | FIG. 24b |
| d30 | 6.60 | FIG. 26b |
| d31 | 2.20 | FIG. 26b |
| d32 | 3 | FIG. 26b |
| d33 | 39-54 | FIG. 30b |
| d34 | 6 | FIG. 30b |

Dimensions di are only illustrative. Any suitable dimensions may be used for features of medicament delivery device 100 (shown in FIGS. 1 and 2), medicament delivery device 2800 (shown in FIGS. 28 and 29) and medicament delivery device 3100 (shown in FIG. 31). Ratios dj:dk and any other suitable ratios of dimensions di may be employed.

Thus, apparatus and methods for sealing a medicament within a medical delivery device have been provided. Persons skilled in the art will appreciate that the present invention can be practiced by other than the described embodiments, which are presented for purposes of illustration rather than of limitation. The present invention is limited only by the claims that follow.

What is claimed is:

1. A method of lyophilizing and sealing a medicament within a medical. delivery device, themethod comprising:
    placing the medicament into the delivery device;
    engaging an inner wall of the delivery device with a plurality of resilient elongated members that are fixed to a sealing base;
    advancing the members into the device until the base is set apart from the inner wall by a predetermined offset, the base held in place relative to the device onlyby the members;
    lyophilizing the medicament to produce avapor that escapes between the inner wall, the members and the base; and,
    then, further advancing the members until the base seals against the inner wall.

2. A method of lyophilizing and sealing a medicament within a medical delivery device, themethod comprising:
    placing the medicament into the device;
    through an opening of the device, engaging an inner wall of the device with a resilient elongated member that is fixed to a sealing base;
    advancing the member relative to the opening until the base is set apart from the opening by a predetermined offset, the base held in place relative to the device only by the member;
    lyophilizing the medicament to produce avapor that escapes between the inner wall, the member and the base; and,
    then, further advancing the member until the base seals against the inner wall.

3. The method of claim 1 wherein the members:
    are set radially away from a central axis of the base; and
    define, between circumferentially adjacent surfaces of the members, one or more than one void having a circumferential span.

4. The method of claim 3 wherein the predetermined offset is scaled in proportion to a ratio of the circumferential span to a circumference of the base.

5. The method of claim 4 wherein the predetermined offset ranges from about 1-35% of the ratio.

6. The method of claim 4 wherein the predetermined offset ranges from about 31-70% of the ratio.

7. The method of claim 4 wherein the predetermined offset ranges from about 66-99% of the ratio.

8. The method of claim 1 wherein the predetermined offkt is scaled in proportion to a length of longitudinal extension of the members from the base.

9. The method of claim 8 wherein the predetermined offset ranges from about 1-35% of the length.

10. The method of claim 8 wherein the predetermined offset ranges from about 31-70% of the length.

11. The method of claim 8 wherein the predetermined offset ranges from about 66-99% of the length.

12. The method of claim 2 Wherein the member:
    is set radially away from a central axis of the base; and
    defines, between circumferentially adjacent surfaces of the member, a void having a circumferential span.

13. The method of claim 12 wherein the predetermined offset is scaled in proportion to a ratio of the circumferential span to a circumference of the base.

14. The method of claim 13 wherein the predetermined offset ranges from about 1-35% of the ratio.

15. The method of claim 13 wherein the predetermined offset ranges from about 31-70% of the ratio.

16. The method of claim 13 wherein the predetermined offset ranges from about 66-99% of the ratio.

17. The method of claim 2 wherein the predetermined offset is scaled in proportion to a length of longitudinal extension of the member from the base.

18. The method of claim 17 wherein the predetermined offset ranges from about 1-35% of the length.

19. The method of claim 17 wherein the predetermined offset ranges from about 31-70% of the length.

20. The method of claim 17 wherein the predetermined offset ranges from about 66-99% of the length.

* * * * *